(12) United States Patent
Puschett

(10) Patent No.: US 7,858,604 B2
(45) Date of Patent: *Dec. 28, 2010

(54) METHOD OF TREATING HUMAN VOLUME EXPANSION MEDIATED HYPERTENSION EMPLOYING RESIBUFOGENIN

(75) Inventor: Jules B. Puschett, New Orleans, LA (US)

(73) Assignee: Scott & White Healthcare, Temple, TX (US)

( * ) Notice: Subject to any disclaimer, the term of this patent is extended or adjusted under 35 U.S.C. 154(b) by 1172 days.

This patent is subject to a terminal disclaimer.

(21) Appl. No.: 11/484,162

(22) Filed: Jul. 11, 2006

(65) Prior Publication Data

US 2007/0014722 A1   Jan. 18, 2007

Related U.S. Application Data

(60) Provisional application No. 60/698,450, filed on Jul. 12, 2005.

(51) Int. Cl.
*A61K 31/56* (2006.01)
*A61K 31/58* (2006.01)

(52) U.S. Cl. .................. 514/170; 514/172; 514/26; 514/25

(58) Field of Classification Search ................ 514/170, 514/172, 26, 25
See application file for complete search history.

(56) References Cited

U.S. PATENT DOCUMENTS

| 4,380,624 | A | * | 4/1983 | Wiesner et al. ............. 536/5 |
| 5,770,376 | A | | 6/1998 | Bagrov |
| 6,251,611 | B1 | | 6/2001 | Puschett |
| 2008/0261928 | A1 | * | 10/2008 | Puschett .................. 514/170 |

FOREIGN PATENT DOCUMENTS

WO    WO 2006/120472 A2    11/2006

OTHER PUBLICATIONS

U.S. Appl. No. 09/990,432, filed Nov. 21, 2001, Jules B. Puschett.
U.S. Appl. No. 10/109,203, filed Mar. 28, 2002, Jules B. Puschett.
U.S. Appl. No. 60/444,730, filed Feb. 4, 2003, Jules B. Puschett.
U.S. Appl. No. 60/619,969, filed Oct. 19, 2004, Jules B. Puschett.
U.S. Appl. No. 60/698,450, filed Jul. 12, 2005, Jules B. Puschett.
Chen et al., "Volume Expansion-Induced Changes in Renal Tubular Membrane Protein Phosphorylation", Biochem. Biophys. Res. Commun. 143:pp. 74-80 (1987).
Pridijian et al., "Neutralization of marinobufogenin normalizes blood pressure in a rat model of preeclampsia", J Soc Gynecol Invest 11(Suppl):260A, 2004.
Cai et al., "Down-Regulation of Phosphorylation of Renal Proximal Brush Border Membrane Protein in DOCA-Salt Hypertensive Rats", J Am Soc Nephrol 5:S26 (1994).
Vu et al., "Involvement of Marinobufagenin in a Rat Model of Human Preeclampsia", Am J Nephrol 2005;25:520-528 (2005).
Vu et al., "Resibufogenin reduces blood pressure in a rat model of preeclampsia", Journal of Investigative Medicine, vol. 53, No. 2, Mar. 2005, p. S367.
Lanz et al., "Angiotensin II regulates 11beta-hydroxysteroid dehydrogenase type 2 via AT2 receptors", Kidney International, vol. 64, No. 3, Sep. 2003, pp. 970-977.

* cited by examiner

*Primary Examiner*—Jennifer M Kim
(74) *Attorney, Agent, or Firm*—Eckert Seamans Cherin & Mellott, LLC; Carol A. Marmo, Esquire

(57) ABSTRACT

A method of treating volume expansion mediated hypertension including administering a therapeutically effective dose of resibufogenin to a patient having volume expansion mediated hypertension. A method for the determination of the presence of volume expansion mediated hypertension may be by determining whether there has been a substantial elevation in marinobufagenin which may be blood-derived or urine-derived and if such elevation does exist, concluding that volume expansion mediated hypertension does exist. The method may advantageously be practiced by employing urine, blood serum or blood plasma as the body specimen in determining whether a patient has volume expansion mediated hypertension. In another embodiment, bufodienolide derivatives other than resibufogenin may be employed in lieu of thereof or in combination therewith. In another embodiment, resibufogenin analogues may be employed in the treatment of volume expansion mediated hypertension.

9 Claims, No Drawings

METHOD OF TREATING HUMAN VOLUME EXPANSION MEDIATED HYPERTENSION EMPLOYING RESIBUFOGENIN

CROSS-REFERENCE

This application claims the benefit of U.S. Provisional Patent Application Ser. No. 60/698,450 filed Jul. 12, 2005, with the U.S. Patent and Trademark Office entitled: "METHOD OF TREATING HUMAN VOLUME EXPANSION MEDIATED HYPERTENSION EMPLOYING RESIBUFAGENIN".

BACKGROUND OF THE INVENTION

1. Field of the Invention

The present invention provides a method for treating a patient that has volume expansion mediated hypertension and, more specifically, it provides such a method which employs resibufogenin in treating volume expansion mediated hypertension.

2. Description of the Prior Art

Elevated blood pressure or hypertension has long been recognized as a health problem. It is a very common disease which can have widespread effects on a patient's body and frequently, unlike numerous other diseases, is asymptomatic.

Despite known means of measuring blood pressure of a patient as by a sphygmomanometer, for example, there is lacking an effective means of detecting the presence of volume dependent hypertension involving higher arterial blood pressure by use of a body specimen, such as blood serum or blood plasma and if it exists treating the same.

From a pathogenetic standpoint, essential hypertension may be divided into two broad categories: (a) volume expansion hypertension, and (b) vasoconstriction hypertension. It has been estimated that about 30 to 40 percent of human essential hypertension may be etiologically related to volume expansion hypertension, especially in certain demographic groups. Previous studies participated in by the present inventor have demonstrated an alteration in the phosphorylation of a proximal tubular membrane protein following acute saline expansion of the experimental rat (Puschett et al. Volume Expansion Induced Changes in Renal Tubular Membrane Protein Phosphorylation, Biochem. Biophys. Res. Commun., 143:pp. 74-80 (1987)).

U.S. Pat. No. 5,770,376 discloses the use of a blood or urine specimen in diagnosing hypertension as an indication of acute myocardial infarction. It employs plasma and/or levels of a marinobufagenin-like immunoreactivity as a marker for hypertension.

Abandoned U.S. patent application Ser. No. 10/109,203 discloses a substantial reduction in phosphorylation or concentration of a specific protein obtained from a body specimen to determine the presence of volume expansion mediated hypertension. See also U.S. Pat. No. 6,251,611.

Abandoned U.S. patent application Ser. No. 09/990,432, filed Nov. 21, 2001, in the name of the present inventor, the disclosure of which is expressly incorporated herein by reference, discloses the use of the CLAMP protein in effecting a determination of the presence of chronic volume dependent hypertension.

Abandoned U.S. Patent Application Ser. No. 60/444,730, filed Feb. 4, 2003, in the name of the present inventor, the disclosure of which is expressly incorporated herein by reference, discloses the use of elevation of marinobufagenin in a body specimen of a pregnant woman to determine whether the patient has volume expansion mediated hypertension.

There remains, therefore, a very real and substantial need for a method for effectively treating volume expansion mediated hypertension.

SUMMARY OF THE INVENTION

The present invention has met the above-described need by providing a method of treating volume expansion mediated hypertension.

Prior to treatment, the determination of the presence of volume expansion mediated hypertension in a patient may involve determining whether there is a substantial elevation in marinobufagenin in blood-derived or urine-derived specimens and, if such elevation does exist, concluding that volume expansion mediated hypertension exists.

A therapeutically effective dosage of resibufogenin may be administered orally or parenterally.

It is an object of the present invention to provide a method for effectively treating human volume expansion mediated hypertension in a reliable and rapid manner.

It is a further object of the invention to determine the presence of volume expansion mediated hypertension at a sufficiently early time as to facilitate early intervention and to prevent a patient's becoming preeclamptic.

It is yet another object of the present invention to employ resibufogenin in the treatment of human volume expansion mediated hypertension.

It is a further object of the present invention to determine the presence of volume expansion mediated hypertension by the elevation in marinobufagenin in a body specimen of a patient followed by subsequent treatment of the patient with resibufogenin.

These and other objects of the invention will be more fully understood from the following description of the invention.

DESCRIPTION OF THE PREFERRED EMBODIMENTS

As used herein, the term "patient" refers to members of the animal kingdom including human beings.

The term "body specimen" means a specimen obtained from a patient which contains marinobufagenin and expressly includes blood serum, blood plasma and urine.

As employed herein, a reference to determining "volume expansion mediated hypertension" means that form of hypertension which is characterized by the expansion of extracellular fluid volume, a consequence of the patient having an excess of salt and water in the body. This type of hypertension is distinguished from the type involving excessive constriction of the blood vessels leading to an increase in peripheral arterial resistance.

The term "substantial elevation" as referred to marinobufagenin concentration as employed herein means an elevation above the normally anticipated range of marinobufagenin in a pregnant person.

Preeclampsia is an example of volume expansion mediated hypertension differing from that seen in any essential hypertension only in that the kidney is under stress related to the pregnancy. Volume expansion mediated hypertension is, however, a broader concept than the species encountered with preeclampsia and eclampsia. The treatment of preeclampsia is disclosed in my Provisional Application Ser. No. 60/619,969, the disclosure of which is expressly incorporated herein by reference. Patients may have a genetic or acquired defect in the ability of their kidneys to excrete a sodium load. This deficiency may not become evident until the patient experiences the stress associated with pregnancy. As they are unable to excrete salt normally they develop volume expansion mediated hypertension. As a result of this deficiency in sodium transport in their kidneys, the salt tends to accumulate thereby causing hypertension and edema. This volume expansion is believed to cause the elaboration of the natriuretic factor known as marinobufagenin, which is employed in the present invention as a marker for diagnosing volume expansion mediated hypertension, as well as being employed in the apparatus and therapeutic method of the present invention.

Marinobufagenin is a cardiotonic steroid which has vasoconstrictor and natruretic properties. Its ability to cause increased sodium excretion is thought to reside in its capability to inhibit the enzyme Na/K ATPase. It is unable to cause the excess sodium to be excreted as a result of the deficiency referred to herein above in the sodium transport pathway.

In the volume expansion mediated hypertension of preeclampsia, the fluid is mostly in the interstitial space where it has leaked from the intravascular space. It is believed by the present inventor that the circulating factor has a role in this "leakiness" of the vascular tree. The uterine vasculature of the preeclamptic patient is characterized by the failure of the decidual small arterioles to dilate normally thereby resulting in large bore, low resistance channels that nourish the placenta and fetus. Instead, these arterioles remain small diameter, high resistance vessels, a condition that is believed by the present inventor to result from the effects of the circulating factor. The net result is that decreased uteroplacental perfusion occurs causing intrauterine growth restriction, prematurity, and fetal wastage.

The preferred practice of the present invention for determining the presence of volume expansion mediated hypertension includes determining if there has been a substantial elevation in marinobufagenin concentration of the blood-derived or urine-derived specimen. The base line for such evaluations may be obtained through evaluation of normal human patients. If such elevation of marinobufagenin does exist, it is concluded that volume expansion mediated hypertension exists. The method provides a method capable of making this determination independently of whether vasoconstriction hypertension or other types of hypertension also exist in the patient.

In general, it is preferred that a substantial elevation in marinobufagenin from normal range be deemed to be at least about a 50 percent elevation in marinobufagenin concentration above the limit of the range of normal human patients before it is determined that volume expansion mediated hypertension exists, and preferably an elevation in the range of at least about 100 to 200 percent elevation. This elevation is ascertained by determining the marinobufagenin concentration of the patient's body and comparing it with an established normal specimen range.

The body specimen employed in practicing the method of the present invention may advantageously be urine or a blood-derived specimen, such as blood serum or blood plasma.

Experiments performed by the present inventor have demonstrated that MGB plays a significant role in the pathogenesis of the preeclamptic syndrome that have been induced in the rat model ("Neutralization of marinobufagenin normalizes blood pressure in a rat model of volume expansion mediated hypertension", Pridjian G et al., J Soc Gynecol Invest, 11(Suppl):260A, 2004) ("The involvement of marinobufagenin in a rat model of volume expansion mediated hypertension", Vu H. et al. [submitted for publication]). Resibufogenin is an analogue of marinobufagenin which has been found not to be biologically active as an antiangiosis agent. This agent is structurally similar to MGB, except that it has a 5-beta hydroxyl group on the B ring of the compound. It is believed that resibufogenin serves as an antagonist to marinobufagenin, probably by displacing marinobufagenin from its receptors in a process of competitive inhibition.

Example

In order to confirm the effectiveness of resibufogenin in treating volume expansion mediated hypertension, experiments were performed. Animal models of volume expansion mediated hypertension were created in the laboratory in accordance with guidance provided in "Down-regulation of Phosphorylation of Renal Proximal Brush Border Membrane Protein in DOCA-salt hypertensive rats". H. Cai et al., J Am Soc Nephrol 5:S26, (1994). These models consisted of the administration of a potent mineralocorticoid desoxycorticosterone (DOCA) to rats whose drinking water had been replaced with 0.9% saline and which had one kidney removed (uninephrectomy) in order to induce volume expansion mediated hypertension. This group of animals is listed as Group I. Group II was the uninephrectomy control group ("time control"). Another group (Group III) utilized the Goldblatt 2 kidney, 1 clip model to induce vasoconstrictive (renin-angiotensin mediated) form of essential hypertension. All of the blood pressures were measured in mm Hg.

In each group, a baseline blood pressure was taken. This is shown in the first column. Subsequently, 10 days to 2 weeks later, just prior to the introduction of resibufogenin, the blood pressure was measured. This appears in the second column. In the third column, the blood pressure was measured 10 days after administration of resibufogenin. The rats in Groups I and III weighed about 200 to 250 gm with resibufogenin being administered in the amount of about 1.53 micrograms per 100 grams of body weight. It will be noted that in each of the four rats in Group I, 10 days after administration of resibufogenin, there was a very substantial reduction in blood pressure. It is also noted that in the Group II control, that there was no meaningful pattern of reduction in blood pressure. Finally, as to Group III, only two rats were tested and neither responded to the resibufogenin.

| | Blood Pressure (mmHg) | | |
|---|---|---|---|
| | Baseline | Prior to Resibufogenin | After 10 days of Resibufogenin |
| Group I: DOCA-salt Uninephrectomized Animals: | | | |
| Rat #1 | 90 | 110 | 85 |
| Rat #2 | 110 | 115 | 90 |
| Rat #3 | 100 | 150 | 130 |
| Rat #4 | 95 | 140 | 100 |
| Group II: Uninephrectomy Control: | | | |
| Rat #1 | 120 | 100 | 100 |
| Rat #2 | 95 | 105 | 95 |
| Rat #3 | 100 | 110 | 105 |
| Rat #4 | 90 | 100 | 105 |
| Group III: 2 Kidney 1 Clip Hypertension: | | | |

There were only two rats in this group thus far in which neither animal responded to resibufogenin.

A dosage of approximately 1.53 micrograms of rat weight with the rats weighing in the range of about 200-250 g was employed daily in order to determine the effectiveness of resibufogenin in the treatment of volume expansion mediated hypertension. The dosage was administered intraperitoneally and the rats monitored after about three to four days of treatment. The resibufogenin was administered in a suitable vehicle such as dimethysulfoxide (DMSO). It is noted that after treatment with resibufogenin, all of the rats experienced a substantial reduction in blood pressure.

These tests clearly show a meaningful reduction in blood pressure in the volume expansion form of essential hypertension category due to administration of resibufogenin, a congener of marinobufagenin. The animals which underwent nephrectomy, but received no drugs, showed no consistent change in blood pressure. The dosage was administered intraperitonially and the rats monitored after about three to four days of treatment. The dosage is preferably administered daily in single or multiple doses.

In general, it is preferred to administer resibufogenin orally or parenterally such as by parenteral injection.

While the present description has focused on the preferred use of resibufogenin, it will be appreciated that other bufadienolide derivatives may be employed in lieu thereof or in combination therewith. The application may also be used with resibufogenin analogues.

It will be appreciated that the present invention provides methods for employing a patient's blood or urine and determining whether volume expansion mediated hypertension exists in the patient, thereby permitting appropriate therapeutic measures to be taken. It is preferred in the present invention once there has been confirmation of the existence of human volume expansion mediated hypertension, to treat the patient with a therapeutically effective dose of resibufogenin The invention also contemplates a method for making such determination and providing therapeutic treatment to a patient as by administering appropriate medication preferably resibufogenin with the dosage corresponding to the other health considerations regarding the patent, the severity of the volume expansion mediated hypertension and the health of the patient in any other respects.

Whereas particular embodiments of the invention have been described herein for purposes of illustration, it will be evident to those skilled in the art that numerous variations of the details may be made without departing from the invention as defined in the appended claims.

The invention claimed is:

1. A method of treating human beings for volume expansion mediated hypertension comprising
administering a therapeutically effective dose of resibufogenin in order to reduce the blood pressure of said patient.

2. The method of claim 1 including
prior to treating said patient confirming the existence of volume expansion mediated hypertension in said patient.

3. The method of claim 2 including
administering said resibufogenin parenterally.

4. The method of claim 2 including
administering said resibufogenin orally.

5. The method of claim 3 including
administering said resibufogenin by parenteral injection.

6. The method of claim 1 including
effecting said treatment daily.

7. The method of claim 1 including
effecting said determination of the existence of human volume expansion mediated hypertension through an elevation in marinobufogenin.

8. The method of claim 6 including
administering said treatment daily in a single daily dose.

9. The method of claim 6 including
effecting said treatment daily in multiple daily doses.

* * * * *

UNITED STATES PATENT AND TRADEMARK OFFICE
CERTIFICATE OF CORRECTION

PATENT NO.       : 7,858,604 B2
APPLICATION NO.  : 11/484162
DATED            : December 28, 2010
INVENTOR(S)      : Jules B. Puschett It is certified that error appears in the above-identified patent and that said Letters Patent is hereby corrected as shown below:

On the Title Pg, second column, Item (Primary Examiner), "Jennifer M Kim" should read --Jennifer M. Kim--.
On the Title Pg, second column, Item (57) Abstract, line 15, "of thereof" should read --thereof--.
Column 2, line 66, "patient" should read --patients--.
Column 2, lines 66-67, "experiences" should read --experience--.
Column 3, line 12, "natruretic" should read --natriuretic--.
Column 3, line 58, "have" should read --has--.
Column 3, lines 59-61, "Neutralization of marinobufagenin normalizes blood pressure in a rat model of volume expansion mediated hypertension" should read --Neutralization of Marinobufagenin Normalizes Blood Pressure in a Rat Model of Preeclampsia--.
Column 3, lines 62-64, "The involvement of marinobufagenin in a rat model of volume expansion mediated hypertension" should read --Involvement of Marinobufagenin in a Rat Model of Human Preeclampsia--.
Column 4, line 66, "Down-regulation of Phosphorylation of Renal Proximal Brush Border Membrane Protein in DOCA-salt hypertensive rats" should read --Down-Regulation of Phosphorylation of Renal Proximal Brush Border Membrane Protein in DOCA-Salt Hypertensive Rats--.
Column 4, line 66, "intraperitonially" should read --intraperitoneally--.
Column 5, line 11, "intraperitonially" should read --intraperitoneally--.
Column 5, line 33, "patent" should read --patient--.
Column 6, line 10, "comprising" should read --comprising:--.

Signed and Sealed this
Fourteenth Day of February, 2012

David J. Kappos
*Director of the United States Patent and Trademark Office*